(12) United States Patent
Thomas et al.

(10) Patent No.: US 8,330,809 B2
(45) Date of Patent: Dec. 11, 2012

(54) VISION SYSTEM WITH SOFTWARE CONTROL FOR DETECTING DIRT AND OTHER IMPERFECTIONS ON EGG SURFACES

(75) Inventors: Leslie Philip Thomas, West Bloomfield, MI (US); Nathaniel Barret Brown, Howell, MI (US)

(73) Assignee: FPS Food Processing Systems, B.V., Re Nootdrop (NL)

( * ) Notice: Subject to any disclaimer, the term of this patent is extended or adjusted under 35 U.S.C. 154(b) by 937 days.

(21) Appl. No.: 12/365,364

(22) Filed: Feb. 4, 2009
(Under 37 CFR 1.47)

(65) Prior Publication Data
US 2009/0195648 A1    Aug. 6, 2009

Related U.S. Application Data

(60) Provisional application No. 61/025,973, filed on Feb. 4, 2008.

(51) Int. Cl.
*H04N 9/47* (2006.01)
*H04N 7/18* (2006.01)

(52) U.S. Cl. ............................... 348/89; 348/91; 348/92

(58) Field of Classification Search .................... 348/89, 348/159, 91, 92
See application file for complete search history.

(56) References Cited

U.S. PATENT DOCUMENTS

| | | |
|---|---|---|
| 2,731,146 A | 1/1956 | Page |
| 2,998,969 A | 9/1961 | Page at al. |
| 3,118,548 A | 1/1964 | Bliss et al. |
| 3,139,176 A | 6/1964 | Bliss |
| 3,169,354 A | 2/1965 | Bliss at al. |
| 3,426,894 A | 2/1969 | Page |
| 3,656,794 A | 4/1972 | McCord |
| 4,591,723 A | 5/1986 | Akiyama |
| 4,872,564 A | 10/1989 | van der Schoot |
| 4,972,093 A | 11/1990 | Cochran et al. |
| 5,017,003 A | 5/1991 | Keromnes et al. |

(Continued)

FOREIGN PATENT DOCUMENTS
JP       59151007 A      8/1984
(Continued)

OTHER PUBLICATIONS

Installation and User's Guide, Diamond Dirt Detector (Single Computer) Manual, 4571000 Rev. A, Sep. 9, 2003, pp. 26, 73.

(Continued)

*Primary Examiner* — Kristie Shingles
(74) *Attorney, Agent, or Firm* — Gifford, Krass, Sprinkle, Anderson & Citkowski, P.C.

(57) ABSTRACT

A vision system incorporated into an item of egg handling equipment, the system incorporating software control for detecting at least one of color shades and defects on both brown and white eggs. An enclosure incorporates a plurality of high resolution producing cameras, these communicating via cable with a switch to a remote vision PC system. A non-linear shaped diffuser is mounted along an open facing bottom of the enclosure for facilitating uniform lighting throughout an open interior of the enclosure associated with the cameras. The cameras are operable to produce multiple, high resolution images of each of a plurality of eggs continuously transported along the associated egg handling equipment, for classifying types of defects that are allowable and those that must be rejected, as well as assisting in the segregating of the eggs into more consistent shaded groups for eventual packaging.

18 Claims, 7 Drawing Sheets

U.S. PATENT DOCUMENTS

| | | | |
|---|---|---|---|
| 5,030,001 A * | 7/1991 | vande Vis | 356/53 |
| 5,237,407 A | 8/1993 | Crezee et al. | |
| 5,495,337 A | 2/1996 | Goshorn et al. | |
| 5,504,572 A | 4/1996 | Taylor et al. | |
| 6,433,293 B1 | 8/2002 | Bollinger et al. | |
| 6,504,603 B1 * | 1/2003 | Schouenborg | 356/53 |
| 6,535,277 B2 | 3/2003 | Chalker, II et al. | |
| 6,851,834 B2 | 2/2005 | Leysath | |
| 7,019,821 B2 | 3/2006 | Kageyama et al. | |
| 7,084,967 B2 | 8/2006 | Nikoonahad et al. | |
| 7,289,196 B2 | 10/2007 | Reeves et al. | |
| 7,359,116 B2 * | 4/2008 | Kenny | 359/385 |
| 7,878,391 B2 * | 2/2011 | Kalkhoff | 235/98 C |
| 2004/0032280 A1 | 2/2004 | Clark et al. | |
| 2007/0030669 A1 | 2/2007 | Van Soest | |
| 2008/0137325 A1 | 6/2008 | Pastore | |
| 2009/0195648 A1 | 8/2009 | Thomas et al. | |

FOREIGN PATENT DOCUMENTS

| | | | |
|---|---|---|---|
| JP | 62211544 A | 9/1987 | |
| JP | 02260091 A | 10/1990 | |
| JP | 09304284 A | 11/1997 | |
| JP | 10076233 A | 3/1998 | |
| JP | 11118722 A | 4/1999 | |
| JP | 11173996 A | 7/1999 | |
| JP | 11326202 A | 11/1999 | |
| JP | 2000235005 A | 8/2000 | |
| JP | 2000236771 A | 9/2000 | |
| JP | 2001027612 A | 1/2001 | |
| JP | 2001037367 A | 2/2001 | |
| JP | 2004-101204 A | 4/2004 | |
| JP | 2004101204 A | 4/2004 | |
| JP | 2005127720 A | 5/2005 | |
| JP | 2005156396 A | 6/2005 | |
| JP | 2007127467 | 5/2007 | |
| JP | 2007-212155 A | 8/2007 | |
| WO | WO-2005/045406 A1 | 5/2005 | |
| WO | WO-2005045406 A1 | 5/2005 | |
| WO | WO-2006027802 A1 | 3/2006 | |

OTHER PUBLICATIONS

Seemax Brochure (believed to have been offered for sale, publicly used and/or published prior to the filing of this application).

Diamond Automation Division brochure, 1975.

Diamond Automation Division brochure, 1976.

Diffuse Line Scan Lights—DLSL1500 Series, page from www.illuminationcontrol.com website (believed to have been offered for sale, publicly used and/or published prior to the filing of this application).

* cited by examiner

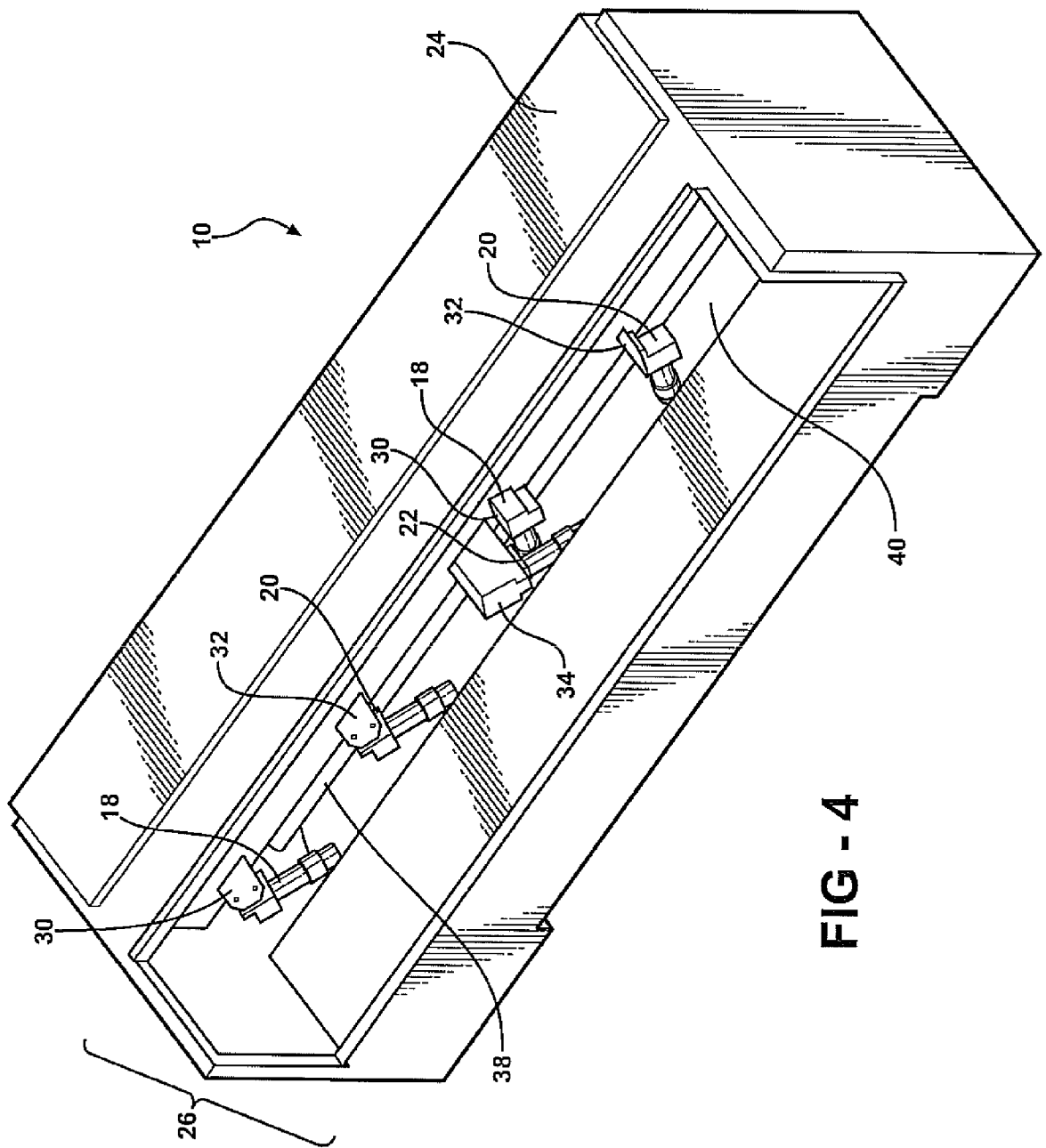

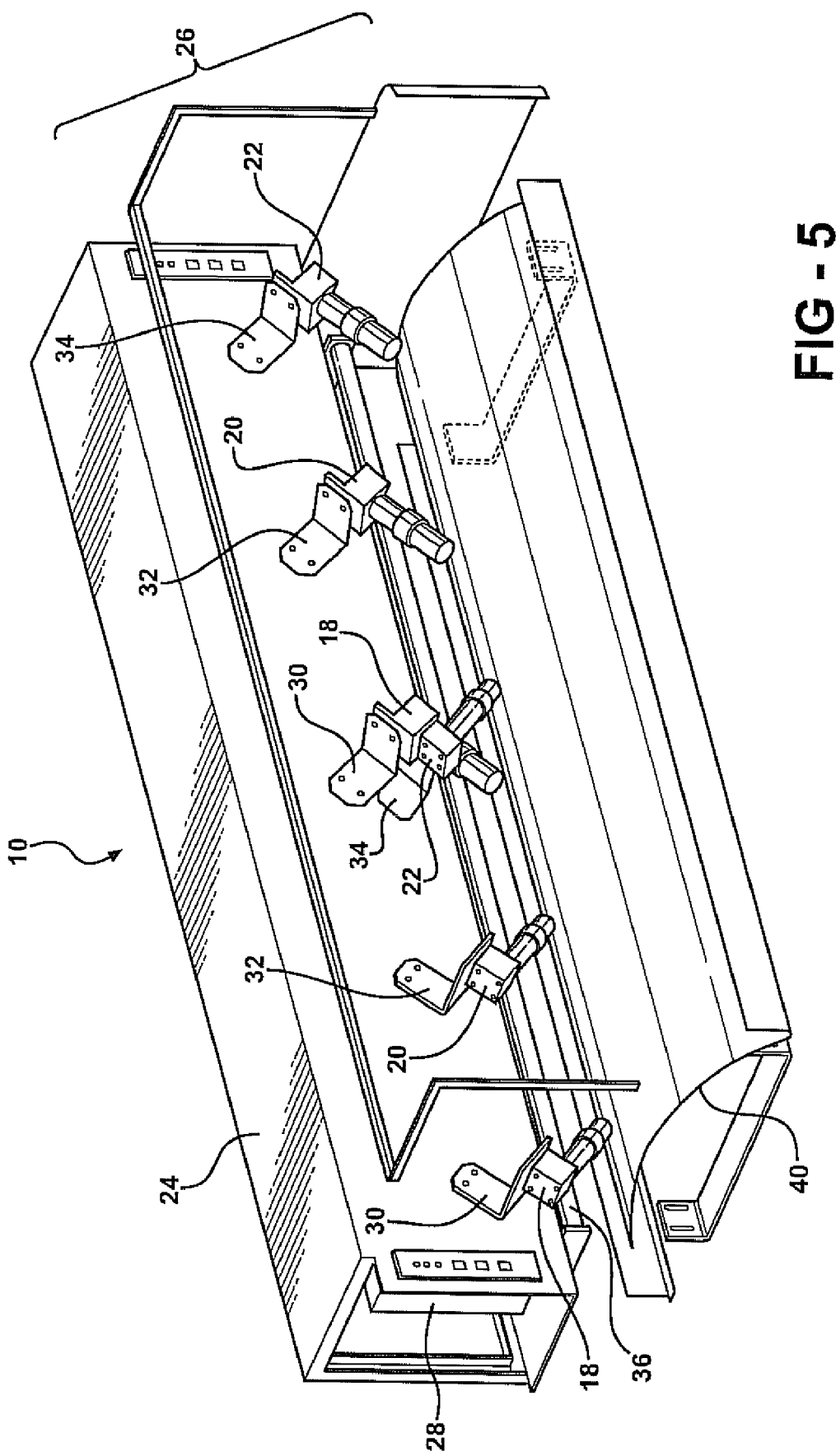

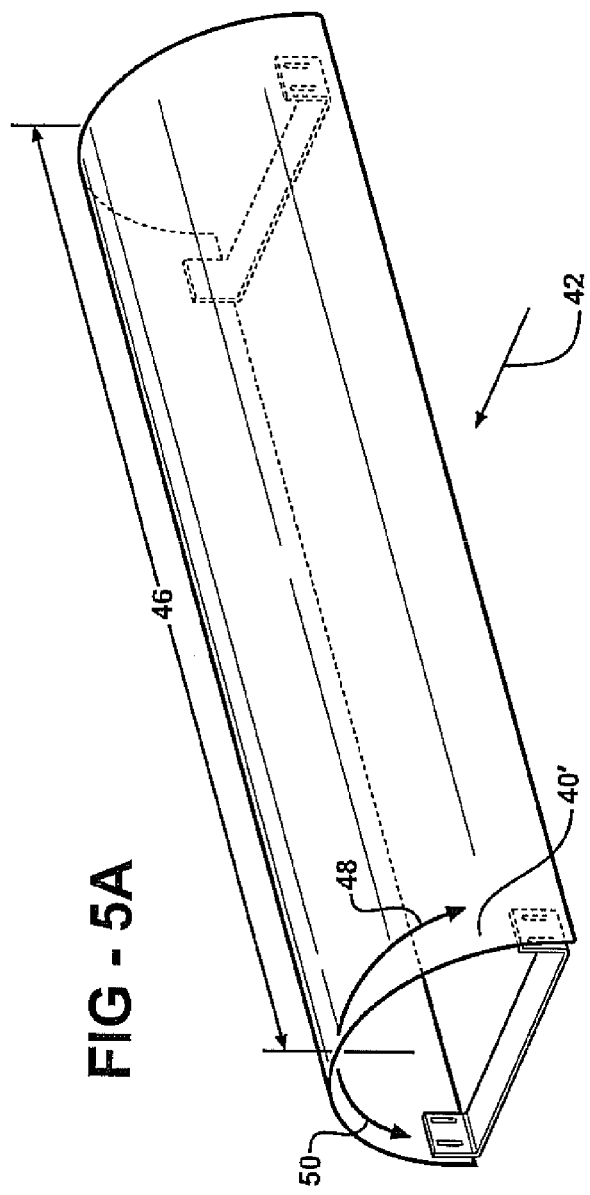
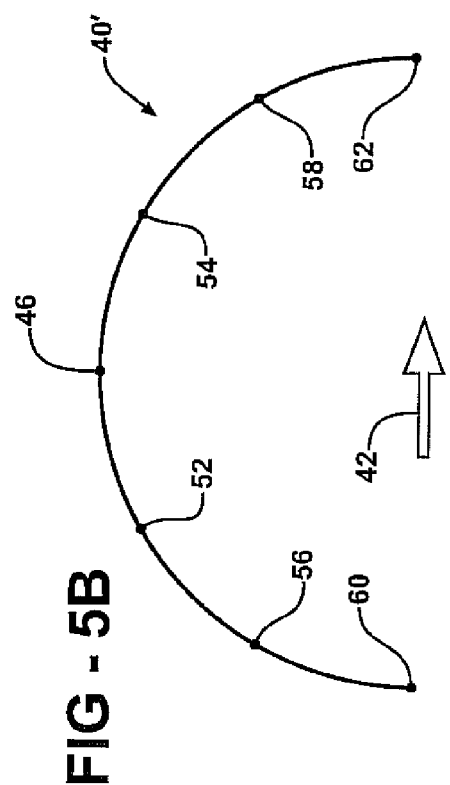
FIG - 5A
FIG - 5B

VISION SYSTEM WITH SOFTWARE CONTROL FOR DETECTING DIRT AND OTHER IMPERFECTIONS ON EGG SURFACES

CROSS-REFERENCE TO RELATED APPLICATIONS

This Application is a Non-Prov of Prov (35 USC 119(e)) application 61/025,973 filed on Feb. 4, 2008 and entitled Vision System with Software Control for Detecting Dirt and Other Imperfections on Egg Surfaces.

FIELD OF THE INVENTION

The present invention teaches a vision system incorporating software control for detecting defects on both brown and white eggs, as well as the ability to detect multiple shades of brown eggs. Specifically, the present invention employs any number of pairs of imaging cameras, such as in particular Ethernet cameras, these being grouped within a three dimensional enclosure that isolates all controlling electrical equipment in a separate sealed section of the unit.

The unit also includes one or more illuminating elements, as well as a curved, arcuate or otherwise non-linear shaped reflector or diffuser element, for redirecting and equally distributing the light generated from the illuminating elements in any of a focused, magnified and evenly distributed fashion within the interior of the unit. The vision system provides, in one non-limiting application, for non-invasive inspection of eggs and in which, by virtue of the ability of the illuminating elements and curved diffuser to uniformly illuminate the area within (as well as optionally below) the unit, this precluding the instance of shadows and other undesirable dark spots, thereby providing for more accurate inspection and detection of egg shades and blemishes.

BACKGROUND OF THE INVENTION

Egg inspection apparatuses are well known in the relevant art. Such apparatuses are often employed in conjunction with varying types of egg processing and transfer equipment, such as conveyors. Typical applications of such devices include the non-invasive inspection of eggs and in order to classify the same, such as by color, size and the like, as well as in detecting unacceptable blemishes associated with such eggs.

One known example of a device for inspecting objects with a spherical surface is set forth in U.S. Pat. No. 7,474,392, to Van Soest, and which a three dimensional box shaped enclosure includes a plurality of upper-most positioned strip lights which illuminate through a matt transparent (e.g. milky like) diffuser plate, and which functions as a top of the box enclosure. A series of four interconnected side and end walls each further exhibit a mirroring inner surface exhibiting a high coefficient of reflection, this causing a constantly recurring light source to be produced for equally illuminating a plurality of objects placed upon a conveyor in communication with an open bottom of the box. One or more cameras are arranged above the conveyors approximate the top inner side walls of the box for observing the objects on the conveyor.

SUMMARY OF THE INVENTION

The present invention discloses a vision system incorporated into an item of egg handling equipment, the system incorporating software control for detecting at least one of color shades and defects on both brown and white eggs. An enclosure incorporates a plurality of high resolution producing cameras (such as Ethernet cameras), these communicating with a gigabit (Ethernet) switch by cable to a remote mounted vision PC system.

A diffuser (also termed a reflective or distribution element) is mounted along an open facing bottom of the enclosure. The diffuser exhibits a curved, arcuate or otherwise non-linear shape, such as including but not limited to a parabolic or like shape, and facilitates uniform lighting throughout an open interior of the enclosure associated with the cameras. A plurality of light producing/illuminating elements are arranged above the diffuser and, in combination with the cameras are operable to produce multiple, high resolution images of each of a plurality of eggs continuously transported along the associated egg handling equipment, such as for classifying types of defects that are allowable and those that must be rejected, as well as assisting in the segregating of the eggs into more consistent shaded groups for eventual packaging.

The cameras can be grouped in any fashion, such as in pairs, such that each camera views a plurality of eggs at a given moment. The associated egg handling equipment can also rotate the egg during the sequence of images taken by the cameras. The illuminating elements are further provided by such as high frequency fluorescent bulbs located along the unit interior. The lighting passes through the customized parabolic, or other non-linear/curved diffuser mounted along an open facing bottom of the unit, for facilitating uniform lighting throughout the unit as well as along the surface area of the conveyor upon which are supported the eggs or other articles to be inspected.

BRIEF DESCRIPTION OF THE DRAWINGS

Reference will now be made to the attached drawings, when read in combination with the following detailed description, wherein like references refer to like parts throughout the several views, and in which:

FIG. 4 is a rotated and further assembled top perspective of the vision system shown in FIG. 1;

FIG. 5 is slightly rotated exploded perspective in comparison to that shown in FIG. 3;

FIG. 5A is a partial illustration of a modified and dome shaped diffuser element according to a further variant;

FIG. 5B illustrates the logarithmic function associated with a cross section of the dome shape diffuser and including parabolic components extending in opposite fashion from the top center lie, linear components extending from end points of the parabolic components, and logarithmic components extending from end points of the linear components to side extending edges of the diffuser.

DETAILED DESCRIPTION OF THE PREFERRED EMBODIMENTS

Referring to the several illustrations presented herein, a vision system 10 is disclosed, such as for detecting defects on both brown and white eggs, as well as the ability to detect multiple shades of brown eggs. As will be subsequently described in further detail, the vision system 10 incorporates machine vision inspection technology, such further understood to include any suitable processor or hardware based support and exhibiting the ability to interface with associated computer related software products, as well as a custom designed element or diffuser (e.g. parabolic and dome shaped as in the examples illustrated) component built into the system for facilitating uniform lighting throughout the assembly.

Figure 6:
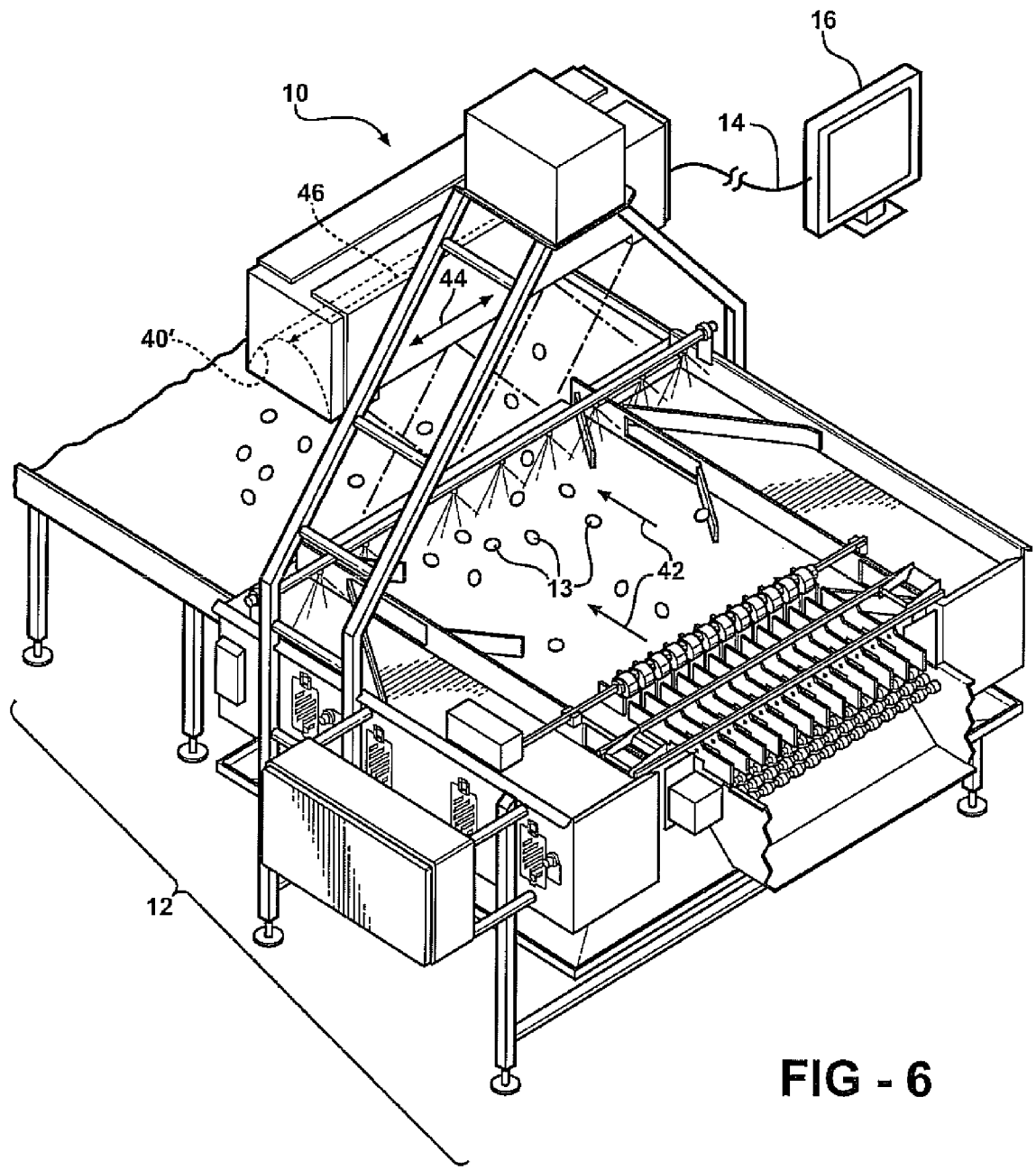
FIG. 6 is a perspective illustration of the vision system mounted to an existing piece of egg handling equipment, and such as including an egg conveyor which is mounted a distance below an overhead suspended vision system, such further illustrating an Ethernet cable extending from the three dimensional unit and connecting to a vision PC at a remote location.

As further referenced in the environmental illustration of FIG. 6, a perspective illustration is shown of the vision system mounted to an existing piece of egg handling equipment, collectively referenced at 12, and by example illustrating an egg orienting and accumulating system used in transporting large numbers of eggs (see at 13), such as from and along a central conveying belt into single file lanes, and for subsequent transfer onto spool bars for delivery to such as another conveyor, egg washer application or the like. For purposes of ease of illustration, the various features associated with the egg conveying/handling equipment 12 (these themselves not being the focus of the invention) are not further referenced or described.

Also illustrated at 14 is an Ethernet cable extending from the three dimensional unit 10, and which is the focus of the present invention, and connecting to a vision PC 16 at a remote location, the functioning of which being described below in further detail. As further referenced above, the vision system incorporates an inspection sub-system the technology for which including adequate hardware and processor components (generally referenced as being included within PC 16) and in order to provide the suitable operating protocol for establishing the inspection parameters of the eggs 13 or other transported objects, such parameters again understood as including shading, determining the existence of spots/blemishes as well as the ability to identify other potential metrics and/or imperfections.

The term "Ethernet", as used in the present application, refers to a family of frame-based computer networking technologies for local area networks (LANs). The name comes from the physical concept of the "ether" and defines a number of wiring and signaling standards, through means of network access of a Media Access Control (MAC)/Data Link Layer, and a common addressing format. In this fashion, Ethernet stations communicate by sending each other data packets, these consisting of individual blocks of data that are individually sent and delivered. As with other LANs, each Ethernet station is given a single 48-bit address, which is used both to specify the destination and the source of each data packet.

As illustrated in each of FIGS. 1-5, the disclosed embodiments includes pairs of Ethernet communicable digital cameras which are grouped within the three dimensional enclosure defining the vision system 10, and as further referenced by individual pairs of opposing arrayed cameras 18, 20 and 22. According to a preferred embodiment, the individual groupings of the cameras (e.g. again at 18, 20 and 22) can be in any fashion, such as in respective pairs which are positioned so that their respective fields of view intersect at given locations (see in particular FIG. 2), and in order that each camera views a plurality of eggs at a given moment, such as in one desired variant with each camera viewing up to twenty eggs (or more). It is further understood that any plurality of cameras, including a single camera or other off number of cameras, can be suitably employed in any variation according to the present inventions and for functioning in the manner described and claimed herein.

It is also noted that, while Ethernet communicable cameras are disclosed in one preferred embodiment, other potential imaging devices, including other acceptable versions of digital cameras operating under different communication platforms, can also be utilized in the incorporation of a modified vision system such perhaps not requiring an Ethernet connection, and without departing from the scope of the invention. Along these lines, the use of an Ethernet cable 14 can be substituted with other cabling or, in certain instances, wireless connectivity established between various (paired) cameras with associated processor controls, incorporated into the cameras or associated components.

In this fashion, each camera can provide a plurality of individual images (such as up to ten or more) per egg. The associated egg handling equipment (again FIG. 6), can also rotate the egg during the sequence of images taken by each of the paired camera(s) 18, 20 and 22. The opposing and angled arrangement of the camera pairs 18, 20 and 22, illustrated in FIGS. 1-5 is further suggestive of one possible arrangement of cameras, it further being understood that any reconfiguration of such cameras is contemplated, and such that either single or multiple (three or more) cameras can be adapted into a desired arrangement and, in cooperation with the performance aspects of the associated egg handling equipment, can provide both a desired number of images and associated degree of resolution of multiple items to be imaged (e.g. eggs).

Within the three dimensional vision system enclosure, a subset and sealed enclosure 24 is provided separately from a frame constructed and generally interiorly open and adjoining enclosure, generally defined at 26. The sealed enclosure 24 isolates all controlling electrical equipment (see as referenced at 28 in the partially stripped away view of FIG. 2 and exploded illustrations of FIGS. 3 and 5) in a separate sealed section of the overall assembly 10.

Figure 1:
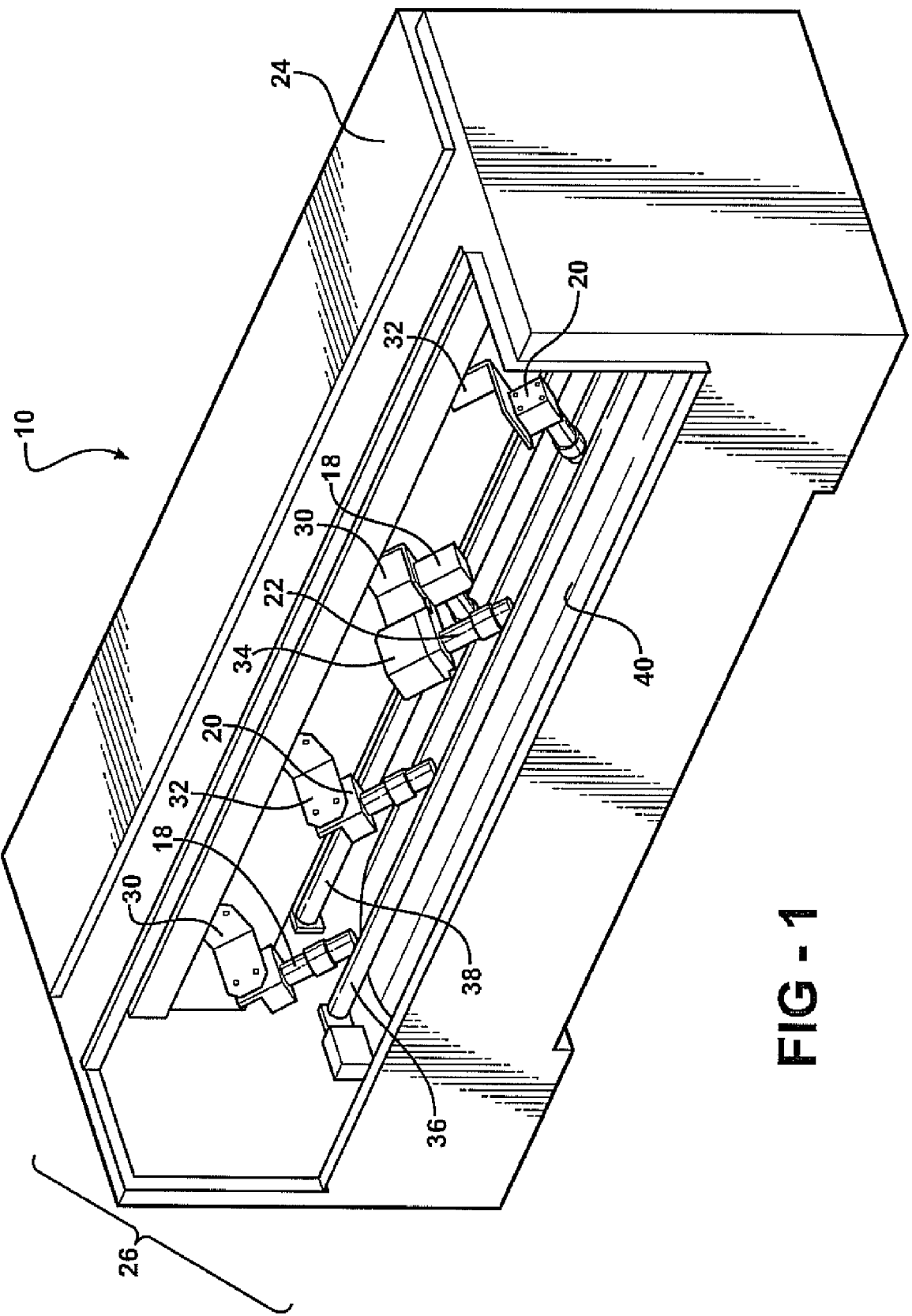
FIG. 1 is a perspective and assembled illustration vision system according to the present invention and exhibiting the three dimensional enclosure, grouped pairs of imaging cameras, fluorescent light tubes and downwardly facing parabolic reflector.
Figure 2:
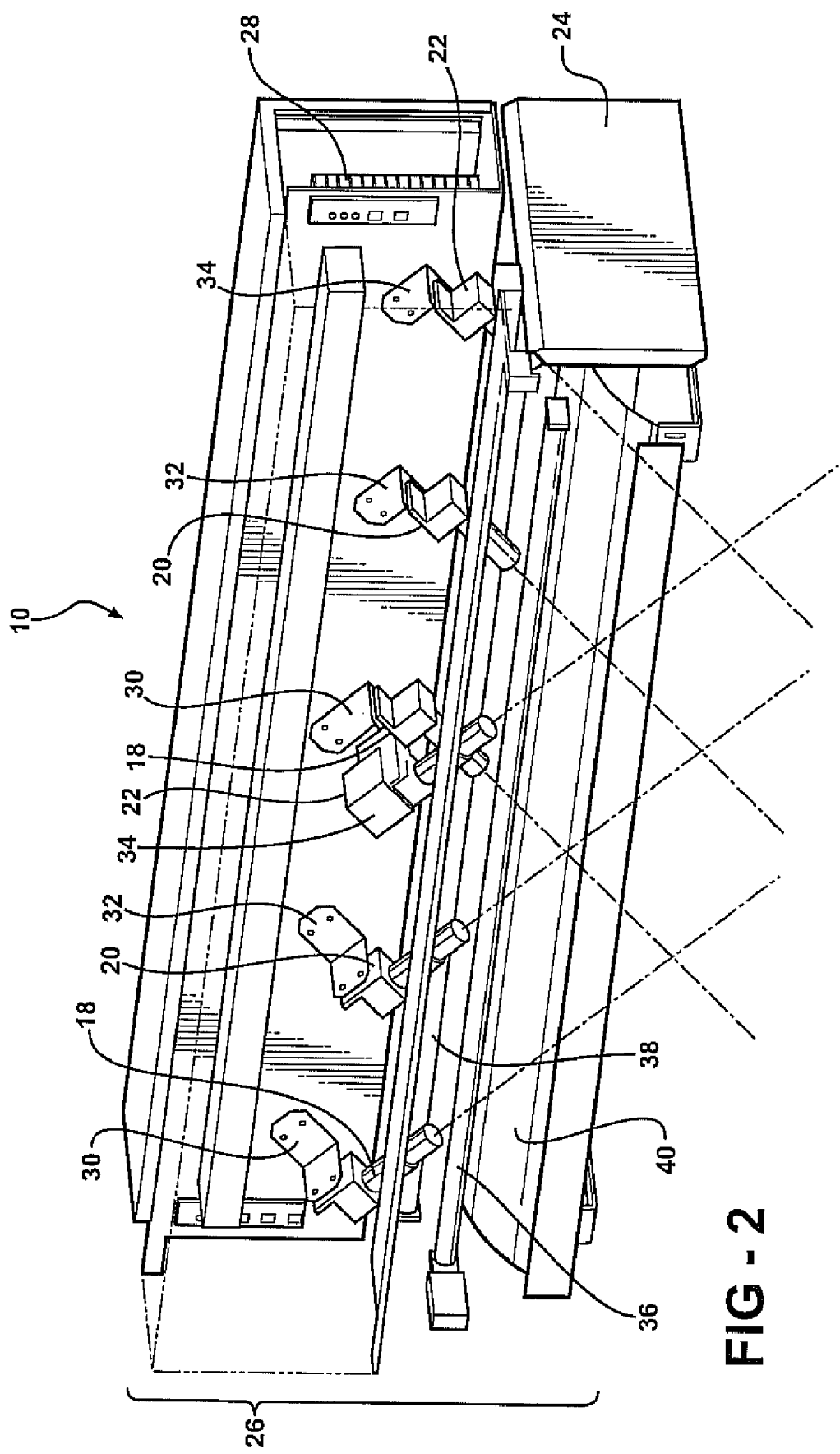
FIG. 2 is a rotated perspective of the vision system and with a selected three dimensional enclosure defining side panel removed in order to better illustrate the arrangement of the cameras, lighting, and parabolic reflector.
Figure 3:
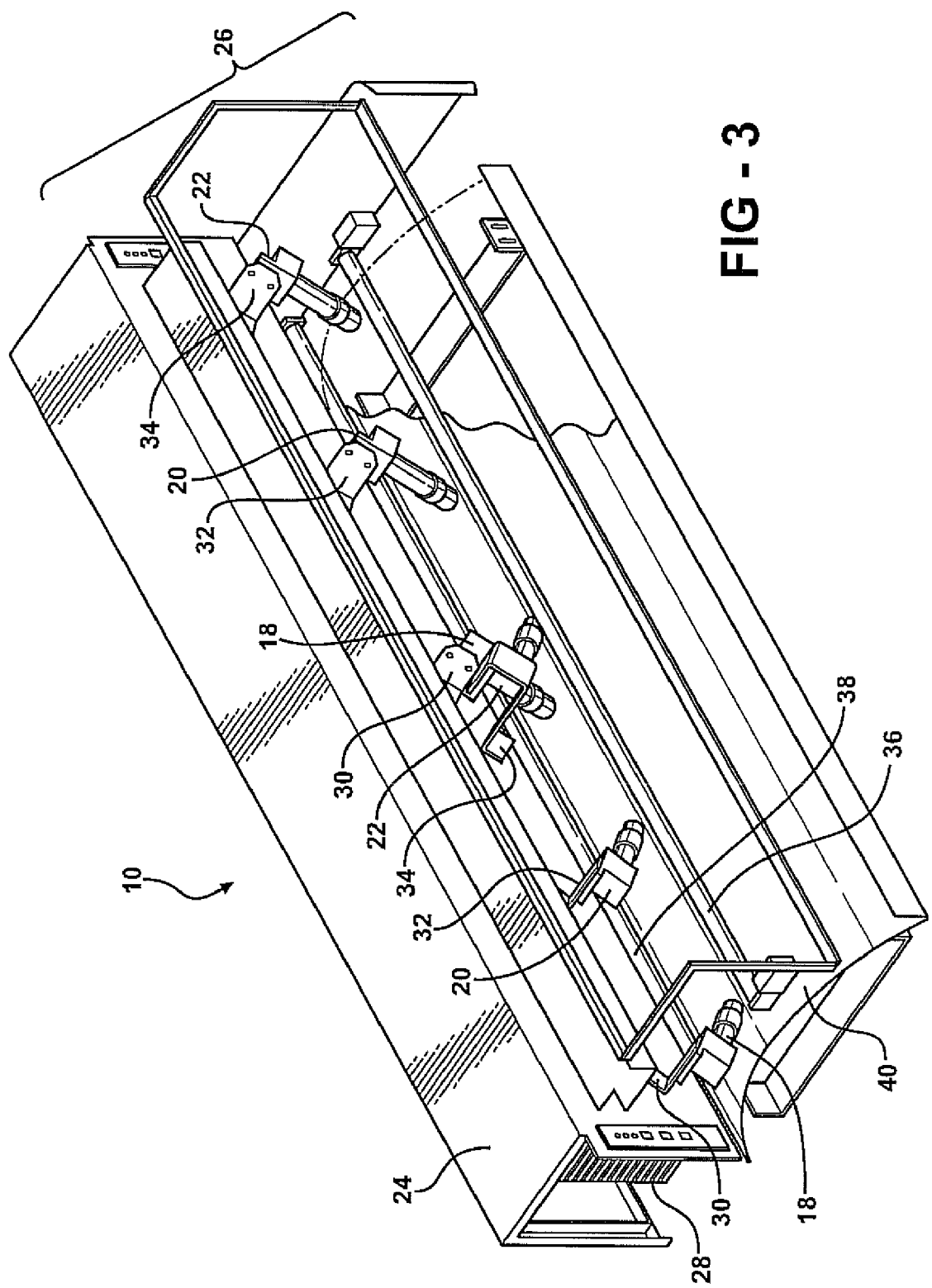
FIG. 3 is a further rotated and partially exploded perspective of the vision system.

As further best shown in FIGS. 2, 3, and 5, the open framed section 26 of the assembly 10 includes a plurality of angled mounting brackets associated with each of the pairs of offset cameras, see as shown at 30, 32 and 34 associated with camera pairs 18, 20 and 22, these mounting the camera pairs such as to surfaces of the sealed electrical containing section 24. Without providing an overly detailed explanation of the mechanical structure for holding together the open framed section 26, a series of frames, braces, and end pieces are illustrated and which are provided for constructing a generally rectangular shaped and open interior three dimensional space, within which the camera pairs are mounted to array in a selected and downwardly angled arrangement.

Unit lighting is provided by any plurality of illuminating elements, and such as which are represented by clear white, high frequency fluorescent bulbs or ballast tubes, referenced as a pair at 36 and 38, this further understood to include such as the provision of any plurality of lighting elements, such as four, six, eight, ten or more fluorescent tubes (in one example each of which being 48" in length apiece) and arranged in spaced and widthwise extending fashion, these utilized for lighting and located along such as an intermediate interior or a bottom facing location of the unit assembly 10. It is further envisioned and understood that the fluorescent bulbs can be substituted by other appropriate lighting elements or sources these including, without limitation, such as L.E.D. (light emitting diode), as well as incandescent or other illuminating elements. Other lighting options include such as employing lasers, and other potential lighting sources can also be incorporated into the assembly 10.

The illumination provided by the illuminating elements passes through a customized non-linear shaped (including arcuate or curved) element, or diffuser, see at 40, and which is mounted along an open facing bottom of the framed and open unit section 26, for facilitating uniform lighting throughout the unit assembly. The configuration of the diffuser element (this term also intended to include any form of light distribution or reflection element the properties of which capable of being separately or concurrently designed into the element 40) in the illustrated embodiment exhibits a pseudo-parabolic shaped diffuser 40.

The reflecting or diffusing capabilities associated with a parabolic shape, according to that provided in the exemplary illustration at 40, typically operate to concentrate light rays (such as generated by the illuminating elements) to a common focal point. The construction of the diffuser as contemplated herein is intended to multiply the focal points to the point of infinity, and so that an even and consistent image pattern is provided both within the three dimensional interior of the unit when the element 40 operates as a reflector component, as well as beneath the unit in a diffusing capacity, and such as along the area upon which the separate conveyor (see as shown in FIG. 6) transports the eggs or other plurality of objects to be inspected. As further described herein, the features of the reflector/diffuser 40 can further be reconfigured such that it provides any desired degree of focusing and magnification, either additionally or alternative to the objective of even distribution of illumination.

Beyond the parabolic configuration shown, the present invention further contemplates the provision of a non-linear element exhibiting any type of curvature or arc, such as shaped according to any mathematical or logarithmic formula for establishing a non-linear surface area, and which facilitates the focusing, even distribution, and/or magnification of the light generated by the illuminating element to the area existing below the unit as well as the surface of the below positioned conveyor. Such other shapes associated with an alternately configured diffuser element can include, in non-limiting fashion, any of an ellipsoidal, geoidal, modified circular, domed or exponentially curved shape for redirecting, according to any desired three dimensional pattern, the direction of the illuminating element rays.

As further referenced in FIG. 5A, the diffuser can further exhibit a substantially dome shape, see at 40', and which is further generally defined in more limiting three dimensional applications as a rounded vault configuration with a generally circular base. The dome shape associated with the element 40' extends in a generally elongated and crosswise fashion similar to that shown in reference to the parabolic shaped element 40 in FIG. 5, the dome shaped diffuser element 40' similarly being shown with open section ends. That said, it is further understood that the ends of the dome shaped diffuser 40' can also be enclosed to exhibit a likewise dome configuration.

Additional features include the dome shaped element extending lengthwise and in a direction perpendicular to the transport direction of the underneath located conveyor (as again clearly shown also in the operational view of FIG. 6 and illustrated by directional arrows 42 extending in a linear direction relative to the egg transport conveyor, and relative to bi-directional arrow 44 identifying the extending direction of the dome shaped diffuser 40', and which is illustrated in phantom in FIG. 6). Additional features include the dome shape exhibiting symmetrical a top center line 46, from which extends first 48 and second 50 extending sides, as shown in FIG. 5A, and which is perpendicular to the transport direction (again directional arrows 42) and which lays in a plane substantially parallel to the transport line (as again shown in FIG. 6). Although not otherwise shown, it is understood that the parabolic shaped diffuser 40 best illustrated in FIG. 5 also includes a similar lengthwise extending top center line, from which extend first and second sides which can be constructed according to a desired mathematical/logarithmic function as will be more completely described below in reference to the dome shape diffuser.

A cross section of the dome shaped diffuser 40' is understood to be perpendicular to the center line 46 and which follows a curve in accordance with any suitable mathematical non-linear function, e.g. any formula or logarithm which results in the creation of a non-linear and three dimensional surface for assisting in the reflection or other redirection (e.g. diffusion) of light. Such mathematical formulations are also understood to employ polynomials, i.e. expressions of multiple algebraic terms such as which contain different powers of the same variable.

As previously described, such mathematical function can also be reconfigured to achieve the previously described parabolic shape, as well as any of an unlimited number of additional configurations. Such additional shapes can include any three dimensional surface exhibiting any number of sides, such as ranging from lesser numbers of defined sides establishing such as any of a range of multi-sided polygons, to significantly greater numbers of sides corresponding substantially to smoother arcuate shapes.

In each instance, such mathematical/logarithmic function is calculated from a center line starting point as shown at 46 in FIG. 5A. It is further understood that the logarithms employed can possess either the same or different mathematically generated functions applied to either of opposite sides of the center line 46, this in order to create the desired three dimensional shaping of the diffuser surface.

Referring to FIG. 5B, an illustration is shown of the logarithmic function associated with a cross section of said dome shape diffuser 40', this shown relative to the conveying direction 42 of the transported items (e.g. eggs 13). The mathematical function includes parabolic components extending in opposite fashion from the top center line 46, and which are defined as being the extending components between top center line 46 to end points 52 and 54. Succeeding linear components extend from the end points 52 and 54 of the parabolic components to further end points 56 and 58. Logarithmic components extend from the end points 56 and 58 of the linear components to the side extending edges of the diffuser, these further defined by terminating points 60 and 62.

The illustrated arrangement of the opposite extending parabolic-linear-logarithmic sequences extending from top center line is understood to depict only one potential mathematical function and that other variations of mathematically constructed curves are also envisioned, such as which can reverse or modify the sequence described in FIG. 5B in any fashion desired, such as further to limit to a lesser number of distinct components or to vary their plurality and/or placement. It is further understood that the mathematical coefficients employed with each of the parabolic, linear and logarithmic functions are capable of being modified to vary the curvature, or to mutate, the profile shown. The ability to modify such functions, on either or both sides of the center line, create the ability to choose coefficients which result in matching variations in pitch such as in the conveyor design. In the instance of the dome surface, it is also understood that the same can be composed of different parts, each of which can be designed to accommodate different operating functions (such as again including variations in reflective and diffusive properties).

The shaping (or reshaping) of the diffuser 40 or 40' again is contemplated to operate in either (or potentially both) a reflective capacity, and in which the interior of the unit is equally illuminated to maximize the efficiency of the cameras, as well as in a diffusing capacity and in which the light can be focused, magnified or otherwise redirected beyond the interior of the enclosure or space located above the diffuser in a desired manner for better illuminating the area beneath the overhead mounted unit (see again FIG. 6) and such as specifically the conveyor upon which the eggs 13 are situated. The ability to establish both increased and balanced illumination of a transport conveyor renders possible the detection of defects associated with wet eggs, historically a very difficult parameter to assess given prior art imaging technologies.

The above-described (paired) cameras are further tied into a gigabit Ethernet switch, again communicated by cable 14 with a remote mounted vision PC system 16. For purposes of a general description, Ethernet technology is most broadly and conventionally defined as a local-area network protocol featuring a bus topology and a 10 megabit per second data transfer rate, this further originally based on the idea of computers communicating over a shared coaxial cable acting as a broadcast transmission medium.

Ethernet stations communicate by sending each other data packets, blocks of data that are individually sent and delivered. In a preferred operation application, data is broken into packets, each of which is transmitted using such as a CSMA/CD algorithm until it arrives at a destination and without colliding with any other packets.

Each Ethernet station is given a single, such as 48-bit, address, which is used both to specify the destination and the source of each data packet. Network interface cards (NICs) or chips normally do not accept packets addressed to other Ethernet stations, and so as to avoid confusion such as between overlapping imaging cameras associated with these protocols.

Advances in Ethernet technology, and in particular the ever-decreasing cost of the hardware needed to support it as well as the reduced panel space it requires, most manufacturers now build the functionality of an Ethernet card directly into PC motherboards, this obviating the need for installation of a separate network card.

In a specified application, the high resolution cameras operate to produce multiple, high resolution images of each of a plurality of eggs continuously transported along the associated egg handling equipment to which the paired (or otherwise arrayed) cameras are mounted. This allows for establishing parameters within the associated PC 16, and such as for detecting both varying shades of brown eggs, as well as for detecting smaller defects on both brown and white eggs. This in turn allows the user more flexibility in classifying the types of defects that are allowable and those that must be rejected, as well as assisting in the segregating of the eggs into more consistent shaded groups for eventual packaging.

It is also understood that, in addition to the software controlling operational protocol described above, the software component of the vision system can be reprogrammed with other criteria or applications, and in order to process, segregate, and accept/reject eggs according to a desired application. Such parameters can include discerning additional and subset color effects and color varieties (and beyond strictly classifying between brown and white eggs). Additional classifications can be accomplished by observing and imaging slime effects, upon wetting the eggs, by yolk and/or albumen.

Having described our invention, other and additional preferred embodiments will become apparent to those skilled in the art to which it pertains, and without deviating from the scope of the appended claims:

We claim:
1. A vision system incorporated into an egg conveying equipment, comprising:
    an enclosure within which is mounted at least one camera;
    an inspection sub-system in communication with said camera; and
    a three dimensional shaped element mounted along a bottom of said enclosure for facilitating at least one of reflective illumination throughout said enclosure and diffusive illumination to an area located beneath said enclosure, said element having a parabolic shape;
    said camera being operable to produce high resolution images of each of a plurality of the eggs continuously transported by the equipment and, in cooperation with said inspection subsystem system, for segregating imaged eggs according to a determined protocol.
2. The vision system as described in claim 1, further comprising a plurality of cameras grouped in opposing arrayed pairs within said enclosure, and further such that each camera views a plurality of objects at a given moment.
3. The vision system as described in claim 2, said enclosure further comprising an interiorly open section within which said cameras are mounted, a second sealed enclosure extending contiguously with said open interior and incorporating controlling electrical equipment.
4. The vision system as described in claim 2, said enclosure exhibiting a specified shape and size and being mounted in overhead arrayed fashion above an egg conveyor translating and/or rotating each of a plurality of eggs during a sequencing of images taken by said cameras.
5. The vision system as described in claim 1, further comprising at least one illuminating element secured within said enclosure, said illuminating element further comprising a plurality of clear white, high frequency fluorescent bulbs.
6. The vision system as described in claim 2, said cameras each further comprising an Ethernet communicable digital camera.
7. The vision system as described in claim 6, said digital cameras communicating with a gigabit Ethernet switch by cable to a remote mounted vision PC system.
8. The vision system as described in claim 7, said cameras producing multiple, high resolution images of each of a plurality of the conveyed objects and which further include a plurality of eggs.
9. The vision system as described in claim 8, further comprising said cameras each generating multiple images of individual eggs and communicable with a software protocol for classifying types of defects in the imaged eggs, as well as assisting in segregating the eggs into more consistent shaded groups.
10. A vision system, comprising:
    an enclosure within which are mounted a plurality of high resolution producing and Ethernet cameras;
    said cameras communicating with a gigabit Ethernet switch by cable to a remote mounted vision PC system;
    a plurality of illuminating elements mounted within said enclosure; and
    a non-linear shaped diffuser exhibiting at least one of a parabolic or dome shape mounted along an open facing bottom of said enclosure for facilitating uniform illumi- nation throughout an open interior of said enclosure associated with said cameras;

said cameras operable to produce multiple, high resolution images of each of a plurality of eggs continuously transported along a surface of an associated item of egg handling equipment for classifying types of defects, as well as assisting in segregating the eggs into more consistent shaded groups.

11. The vision system as described in claim 10, further comprising said cameras grouped in individual and opposingly arrayed pairs contained within said enclosure, such that each camera views a plurality of eggs at a given moment, a second sealed enclosure extending contiguously with said open framed interior enclosure and incorporating controlling electrical equipment.

12. A vision system for inspecting each of a plurality of conveyed eggs, comprising:

a three dimensional enclosure housing a plurality of high resolution cameras, said enclosure being mounted in an overhead and downwardly arrayed fashion relative to a surface upon which the eggs are conveyed;

said cameras communicating with a remote mounted inspection subsystem; and a three dimensional shaped diffuser mounted along an open facing bottom of said enclosure for facilitating dispersal of uniform lighting created within an open interior of said enclosure, said diffuser exhibiting a curvature for establishing a non-linear surface area;

said cameras operable to produce high resolution images of each of a plurality of eggs continuously transported along the egg handling equipment in a travel direction perpendicular to and beneath a linear extending direction of said enclosure, for segregating imaged eggs according to a determined protocol.

13. A vision system incorporated into an egg conveying equipment, comprising:

an enclosure within which is mounted at least one camera;

an inspection sub-system in communication with said camera; and a three dimensional shaped element mounted along a bottom of said enclosure for facilitating at least one of reflective illumination throughout said enclosure and diffusive illumination to an area located beneath said enclosure, said element having a dome shape;

said camera being operable to produce high resolution images of each of a plurality of the eggs continuously transported by the equipment and, in cooperation with said inspection subsystem system, for segregating imaged eggs according to a determined protocol.

14. The vision system as described in claim 13, further comprising said dome shaped element extending in a lengthwise direction which is perpendicular to a travel direction of a conveyor associated with the object conveying equipment.

15. The vision system as described in claim 13, said dome shaped element further comprising first and second symmetrical extending sides extending from a top center line extending perpendicular to a travel direction of a conveyor associated with the object conveying equipment and laying in a plane substantially parallel to a transport plane associated with the conveyor.

16. The vision system as described in claim 15, further comprising a cross section of said dome shaped diffuser being perpendicular to said center line and following a curvature in accordance with a mathematical non-linear function.

17. The vision system as described in claim 16, wherein said mathematical function further comprises a logarithmic function having its starting point on said center line.

18. The vision system as described in claim 17, said logarithmic function associated with a cross section of said dome shape diffuser further comprising at least one of parabolic, linear and logarithmic components extending in opposite fashion from said top center line to side extending edges of said diffuser.

* * * * *

UNITED STATES PATENT AND TRADEMARK OFFICE
CERTIFICATE OF CORRECTION

PATENT NO. : 8,330,809 B2
APPLICATION NO. : 12/365364
DATED : December 11, 2012
INVENTOR(S) : Leslie Philip Thomas et al.

It is certified that error appears in the above-identified patent and that said Letters Patent is hereby corrected as shown below:

In the Specification:

At column 2, line number 60, Delete "top center lie", Insert -- top center line --

Signed and Sealed this
Twenty-third Day of April, 2013

Teresa Stanek Rea
*Acting Director of the United States Patent and Trademark Office*